United States Patent [19]
Sedergran et al.
[11] Patent Number: 4,675,398
[45] Date of Patent: Jun. 23, 1987

[54] COPPER-MEDIATED OXIMATION REACTION

[75] Inventors: Thomas C. Sedergran, Plainsboro; Carl F. Anderson, Milltown, both of N.J.

[73] Assignee: E. R. Squibb & Sons, Inc., Princeton, N.J.

[21] Appl. No.: 766,224

[22] Filed: Aug. 16, 1985

[51] Int. Cl.[4] .................... C07D 417/12; C07D 417/14

[52] U.S. Cl. .................................... 540/355; 540/205; 540/222; 540/225; 540/227; 540/228; 540/301; 540/315

[58] Field of Search ...................... 260/245.4, 245.2 R; 544/22, 25, 27, 28, 90; 540/355, 205, 222, 301, 225, 228, 227, 315

[56] References Cited

U.S. PATENT DOCUMENTS 4,443,374 4/1984 Cimarusti et al. ............. 260/239 A

OTHER PUBLICATIONS

Vowinkel, Chem. Ber. 107, 1221-7 (1974).

*Primary Examiner*—Mark L. Berch
*Attorney, Agent, or Firm*—Lawrence S. Levinson; Donald J. Barrack

[57] ABSTRACT

The presence of a copper salt during the oximation of a $\beta$-lactam containing compound having glyoxylamino substituents of the formula

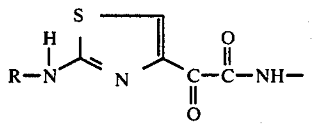

by reaction with an aminooxy compound having the formula $H_2N—O—R_a$, or a salt or ester thereof, results in a product wherein the ratio of syn isomer to anti isomer is increased.

16 Claims, No Drawings

COPPER-MEDIATED OXIMATION REACTION

BACKGROUND OF THE INVENTION

Many β-lactam containing antibiotics have an acylamino side-chain of the formula

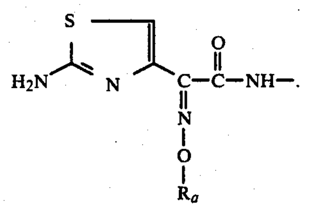

The symbol "$R_a$", as used here and throughout the specification, can be carboxyalkyl (preferably carboxymethyl or 1-carboxy-1-methylethyl). Exemplary antibiotics include aztreonam and ceftazidime. Many processes are described in the prior art for preparing compounds of this type. One such process (see, for example, U.S. Pat. No. 4,443,374) comprises the initial preparation of a compound having the formula

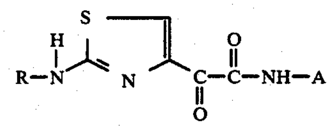

(here and throughout the specification the symbol "A" can be the nucleus of a β-lactam containing antibiotic and the symbol "R" can be an amino protecting group), followed by reaction of that compound with an aminoxy derivative of the formula $H_2N—O—R_a$, followed by deprotection of the resulting compound. This reaction yields a product which exists as the syn or anti isomer or as a mixture of isomers. In the antibiotic art it has been found that the syn isomer exhibits greater activity than the anti isomer.

BRIEF DESCRIPTION OF THE INVENTION

It is an object of this invention to provide a process for preparing β-lactam containing antibiotics which have an acylamino substituent of the formula

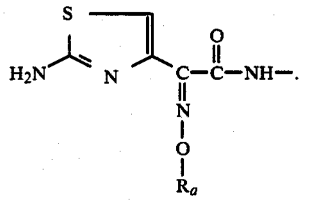

It is a further object of this invention to provide a process for preparing β-lactam containing antibiotics which have an acylamino substituent of the formula

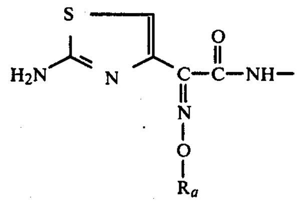

wherein the ratio of syn isomer to anti isomer is maximized.

These, and other objects which will be apparent to the practitioner of this invention, are achieved by the process disclosed herein. The process comprises reacting a compound having the formula

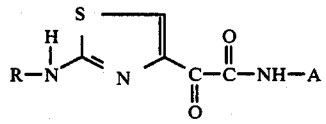

with a compound having the formula $H_2N—O—R_a$, or a salt or ester thereof, in the presence of a copper salt.

DETAILED DESCRIPTION OF THE INVENTION

The use of a copper salt as a mediator for the reaction of a glyoxyl containing compound having the formula

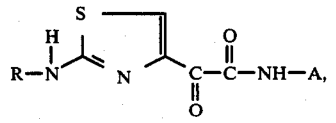

with an aminoxy compound having the formula $H_2N—O—R_a$, or a salt or ester thereof, results in a reaction product having a larger ratio of syn isomer/anti isomer than if the copper salt were not present. Esters of the aminoxy reactant include alkyl ester and substituted alkyl esters. Preferred esters include the methyl, ethyl n-propyl, isopropyl, t-butyl and diphenylmethyl esters.

The above oximation reaction can be carried out in the presence of about 0.5 to 2 equivalents of copper salt based on the glyoxyl reactant, preferably about 0.75 to 1.5 equivalents of copper salt, and most preferably about 1.0 equivalent of copper salt. Any copper salt which is soluble in the solvent system of the reaction can be used. Exemplary solvent systems are water, alcohol-water, dimethylacetamide-water, dimethylsulfoxide-water, acetonitrile-water, tetrahydrofuran-water and acetic acid-water. Exemplary copper salts include cupric halide (e.g., cupric chloride or cupric bromide), cupric sulfate, cupric acetate, cupric nitrate, cupric oxide, cupric carbonate, cupric perchlorate, cupric tetrafluoroborate, cuprous halides (e.g., cuprous chloride or cuprous bromide), cuprous acetate and cuprous oxide.

Upon completion of the copper mediated oximation reaction, the copper ion can be precipitated from solution by the addition of an organic ligand. Exemplary organic ligands are oxalic acid, ethylenediaminetetraacetic acid, and 2,4-pentanedione.

The deprotection of the amino substituent of the thiazole nucleus can be accomplished using art-recognized procedures. If, for example, R is formyl, deprotection can be accomplished by acidification of the reaction mixture to a pH of about 1.0 or less. If an ester of the aminoxy reactant ($H_2N—O—R_a$) is used, the ester group can be cleaved from the reaction product using art-recongized techniques.

It is theorized that the positive effect of the copper salt on the ratio of any isomer/anti isomer arises from a complexing of copper cations with the protected aminothiazole side chain of the ketoamide reactant

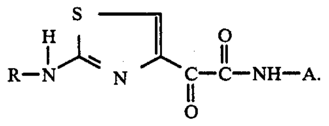

The copper mediation of the oximation reaction can be used with all types of β-lactam containing ketoamide reactants. Exemplary ketoamide reactants are cephalosporins, penicillins, monobactams (i.e., a 2-azetidinone having an $—SO_3H$ activating group in the 1-position; see, for example, United Kingdom patent application No. 2,071,650, published Sept. 23, 1983), monophosphams (i.e., a 2-azetidinone having a phosphorous containing activating group in the 1-position; see, for example, U.S. Pat. No. 4,478,749, issued Oct. 23, 1984), monoxacetams (i.e., a 2-azetidinone having an $—O—CH_2COOH$ activating group in the 1-position; see, for example South African Pat. No. 835470, published Apr. 25, 1984), monosulfactams (i.e., a 2-azetidinone having an $—OSO_3H$ activating group in the 1-position; see, for example, U.S. Pat. No. 4,337,197, issued June 29, 1982) and monocarbams (i.e., a 2-azetidinone having a

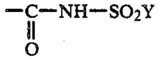

activating group in the 1-position; see, for example, United Kingdom patent application No. 062,876, published Oct. 2, 1982).

Exemplary cephalosporin ketoamide reactants are those having the formula

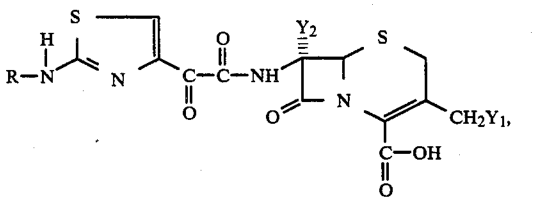

and salts thereof, wherein $Y_1$ is acetyloxy, pyridinium, (4-aminocarbonyl)pyridinium, (1-methyl-1H-tetrazol-5-yl)thio, [1-[2-(dimethylamino)ethyl]-1H-tetrazol-5-yl]thio, [1-(carboxylmethyl)-1H-tetrazol-5-yl]thio, [1-(sulfomethyl)-1H-tetrazol-5-yl]thio, 1H-1,2,3-triazol-4-ylthio, (1,3,4-thiadiazol-2-yl)thio, (5-methyl-1,3,4-thiadiazol-2-yl)thio, or aminocarbonyloxy, and $Y_2$ is hydrogen or methoxy.

Exemplary penicillin ketoamide reactants are those having the formula

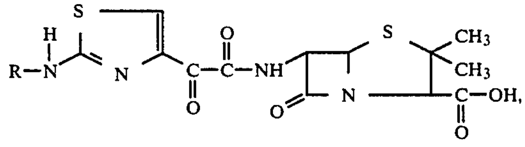

and salts thereof.

Exemplary monocyclic β-lactam ketoamide reactants are those having the formula

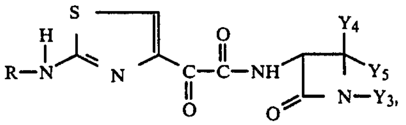

and salts thereof, wherein $Y_3$ is $—SO_3H$ or $—O—SO_3H$ and $Y_4$ and $Y_5$ are each independently hydrogen or alkyl or one of $Y_4$ and $Y_5$ is hydrogen and the other is carbamoyloxymethyl.

The amino substituent on the thiazole nucleus of the ketoamide reactant is protected (the "R" substituent). The expression "amino protecting group" refers to a group that will protect an amine group from involvement in subsequent chemical reactions. Exemplary protecting groups include formyl, t-butyloxycarbonyl, benzyloxycarbonyl, chloroacetyl, and trichloroacetyl.

EXAMPLE 1

Copper Mediated Preparation of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid Aminoxyisobutyric acid (24.9 g, 0.16 mol), copper (II) sulfate pentahydrate (27.4 g, 0.11 mol), and water (300 ml) were placed in a 1 liter, round-bottomed flask equipped with a mechanical stirrer, a pH meter, and a water bath. The pH was adjusted to 2.0 with 50% aqueous sodium hydroxide and (3S-trans)-3-[[[2-(formylamino)-4-thiazolyl]oxoacetyl]amino]-4-methyl-2-oxo-1-azetidinesulfonic acid, potassium salt (50.0 g, 91.4% purity, 0.11 mol) was added with stirring. The reaction as heated to 30° C. and maintained at pH 2.0–2.2 with 50% aqueous sodium hydroxide for 3 hours. At this point, oxalic acid (13.9 g, 0.11 mol) and Darco (5.0 g) were added, and the mixture stirred for 15 minutes. The solution was filtered over Hyflo and the cake washed with water (40 ml). Acidification of the filtrate to pH 0.5 with concentrated hydrochloric acid was followed by heating to 50° C. After 3 hours, the deformylation was complete by in-process HPLC, and the reaction mixture was cooled to 0°–5° C. for 2 hours. Vacuum filtration of the resulting slurry gave a white cake which was washed with cold water until the wash filtrate gave a negative chloride test. The product was dried in a vacuum over for 16 hours at 30° C. to give 44.8 grams of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid.

What is claimed is:

1. In a process for the preparation of a β-lactam containing antibiotic having an acylamino substituent of the formula

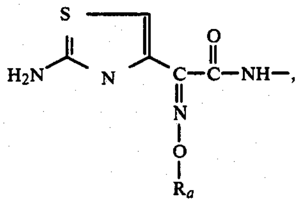

said process comprising the oximation of a $\beta$-lactam containing compound having a glyoxylamino substituent of the formula

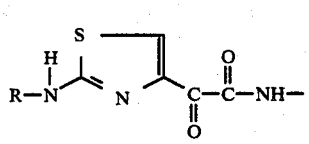

by reaction with an aminoxy compound having the formula $H_2N—O—R_a$, or a salt or ester thereof, the improvement comprising the addition of a copper salt to the reaction mixture; wherein R is an amino protecting group and $R_a$ is carboxyalkyl.

2. A process in accordance with claim 1 wherein $R_a$ is carboxymethyl.

3. A process in accordance with claim 1 wherein $R_a$ is 1-carboxy-1-methylethyl.

4. A process in accordance with claim 1 wherein R is formyl, t-butyloxycarbonyl, benzyloxycarbonyl, chloroacetyl, or trichloroacetyl.

5. A process in accordance with claim 1 wherein R is formyl.

6. A process in accordance with claim 1 wherein the copper salt is a cupric halide, cupric sulfate, cupric acetate, cupric nitrate, cupric oxide, cupric carbonate, cupric perchlorate, cupric tetrafluoroborate, a cuprous halide, cuprous acetate or cuprous oxide.

7. In a process for the preparation of a compound having the formula

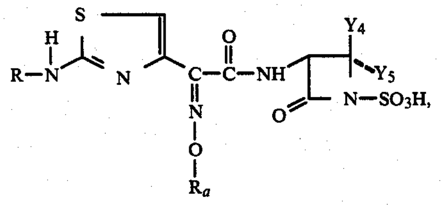

said process comprising the oximation of a compound having the formula

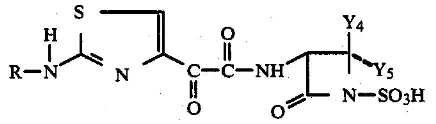

by reaction with an aminoxy compound having the formula $H_2N—O—R_a$, or a salt or ester thereof, the improvement comprising the addition of a copper salt to the reaction mixture; wherein R is an amino protecting group, $R_a$ is carboxyalkyl, $Y_4$ and $Y_5$ are each independently hydrogen or alkyl or one of $Y_4$ and $Y_5$ is hydrogen and the other is carbamoyloxymethyl.

8. A process in accordance with claim 7 wherein $R_a$ is carboxymethyl.

9. A process in accordance with claim 7 wherein $R_a$ is 1-carboxy-1-methylethyl.

10. A process in accordance with claim 7 wherein R is formyl, t-butyloxycarbonyl, benzyloxycarbonyl, chloroacetyl, or trichloroacetyl.

11. A process in accordance with claim 7 wherein R is formyl.

12. A process in accordance with claim 7 wherein the copper salt is a cupric halide, cupric sulfate or cupric acetate.

13. In a process for the preparation of a compound having the formula

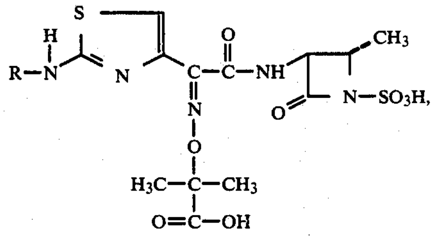

said process comprising the oximation of a compound having the formula

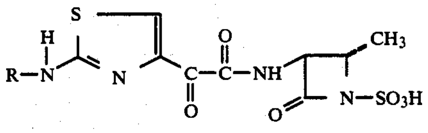

by reaction with an aminoxy compound having the formula

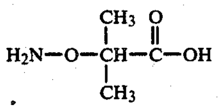

or a salt or ester thereof, the improvement comprising the addition of a copper salt to the reaction mixture; wherein R is an amino protecting group.

14. A process in accordance with claim 13 wherein R is formyl, t-butyloxycarbonyl, benzyloxycarbonyl, chloroacetyl, or trichloroacetyl.

15. A process in accordance with claim 13 wherein R is formyl.

16. A process in accordance with claim 13 wherein the copper salt is a cupric halide, cupric sulfate or cupric acetate, cupric nitrate, cupric oxide, cupric carbonate, cupric perchlorate, cupric tetrafluoroborate, a cuprous halide, cuprous acetate or cuprous oxide.

* * * * *